United States Patent [19]
Buckley et al.

[11] Patent Number: 5,286,415
[45] Date of Patent: Feb. 15, 1994

[54] WATER-BASED POLYMER THICK FILM CONDUCTIVE INK

[75] Inventors: Michael S. Buckley, Diamond Bar; Richard E. Bowns, Hacienda Heights, both of Calif.

[73] Assignee: Advanced Products, Inc., Ontario, Calif.

[21] Appl. No.: 997,374

[22] Filed: Dec. 28, 1992

[51] Int. Cl.$^5$ .................. H01B 1/00; H01B 1/20; H01B 1/22; H01B 1/24
[52] U.S. Cl. .................. 252/502; 252/511; 252/512; 252/514; 252/518; 106/1.18; 106/1.25; 524/501; 524/503
[58] Field of Search .............. 252/502, 511, 512, 514, 252/518; 106/1.18, 1.25; 524/501, 503

[56] References Cited

U.S. PATENT DOCUMENTS

| | | | |
|---|---|---|---|
| 4,011,388 | 3/1977 | Murphy et al. | 524/733 |
| 4,156,047 | 5/1979 | Wysong | 428/220 |
| 4,510,275 | 4/1985 | Ihikura et al. | 524/507 |
| 4,853,285 | 8/1989 | Sobata et al. | 252/511 |
| 4,981,885 | 1/1991 | Engel et al. | 524/460 |
| 5,137,542 | 8/1992 | Buchanan et al. | 252/502 |

*Primary Examiner*—Paul Lieberman
*Assistant Examiner*—M. Kopec
*Attorney, Agent, or Firm*—William A. Simons; Dale L. Carlson

[57] ABSTRACT

The present invention relates to an aqueous conductive polymer thick film-forming composition comprising a water-soluble thermoplastic polymer, a polymer dispersion in water, a glycol drying-retarder agent, an electrically conductive amount of conductive metal and/or carbon particles and water. The composition in the production of a highly printable conductive thick film ink.

8 Claims, No Drawings

WATER-BASED POLYMER THICK FILM CONDUCTIVE INK

BACKGROUND OF THE INVENTION

1. Field of the Invention

This invention relates generally to aqueous polymer thick film conductive compositions containing conductive metal, carbon or graphite particles. The compositions are particularly useful for screening into electrical circuits and for formulation into human contact electrodes.

2. Brief Description of the Art

In the past, water-based conductive polymer thick film formulations have typically exhibited poor rheology, poor adhesion and poor flexibility when printed and cured on polyester or polycarbonate films. They also have not offered the relatively low electrical resistance that is achievable with solvent based formulas.

In view of the above, new aqueous compositions which provide a solution to the above problems while containing a reduced amount of organic solvents, relative to conventional solvent-based thick film formulations, would be highly desired by the polymer thick film manufacturing community. The present invention provides one solution to this problem. This invention relates to the use of water soluble thermoplastic polymers in a water-based polymer thick film-forming compositions to impart smooth, easily spreadable coating qualities to the formulation.

SUMMARY OF THE INVENTION

In one aspect, the present invention relates to an aqueous conductive polymer thick film-forming composition comprising (preferably consisting essentially of):

(a) a water soluble thermoplastic polymer in an amount of between about 0.25% and about 20% by weight (b) a polymer dispersion in water in an amount of between about 10% and about 70% by weight;

(c) a glycol drying-retarder agent(s) in an amount of between about 2% and about 20% by weight;

(d) an electrically conductive amount of conductive particles selected from the group consisting of conductive metal (preferably silver flake), carbon, and graphite particles, and combinations thereof, with the proviso that the amount of said metal particles does not exceed 90 % by weight and the amount of said carbon or graphite particles does not exceed 40% by weight; and (e) water in a solvent effective amount, each of said amounts being based upon the total weight of said composition.

This and other aspects will become apparent upon reading the following detailed description of the invention.

DETAILED DESCRIPTION OF THE INVENTION

In accordance with the present invention, an aqueous conductive polymer thick film-forming film composition is provided which provides excellent film properties, such as resistivity and printability, during use. The compositions provide a distinct advantage from an environmental standpoint since they are water-based. These compositions are useful as highly printable conductive inks utilizing screen printing or other conventional printing method. These inks are of such highly printable quality that lines and spaces 15 mils wide can be clearly printed. This highly printable quality is important in order to effectively print the intricate circuitry patterns often demanded by the electronics industry in high performance applications such as, for example, in the preparation of touch pad circuitry.

Examples of suitable thermoplastic water soluble polymers useful in the present invention include polyethyloxyazoline, polyvinyl pyrrolidone, polyvinyl alcohol, polyacrylamide, polyglycols and polyacrylic acid.

Examples of suitable polymer dispersions in water include polyurethane, acrylic, polyester and vinyl resin polymers.

The purpose of the glycol drying retarding agent(s) employed in the present invention is to slow down the drying process so as to permit manipulation of the polymer thick film, such as by silk screening, before it has a chance to dry. Examples of suitable glycol type drying retarding agents include: diethylene glycol ethyl ether acetate; diethylene glycol butyl ether acetate; ethylene glycol butyl ether acetate; diethylene glycol monoethyl ether; ethylene glycol monoethyl ether; dipropylene glycol methyl ether; tripropylene glycol methyl ether; dibutyl phthalate; diocyl phthalate; diocyl phthalate; tributyl phosphate; 1,3 butylene glycol; propylene glycol and ethylene glycol. These agents may be used singularly or in combination with each other.

Any conductive metal particle may be used in the composition of this invention such as copper, gold, nickel, silver alloys, silver plated metals and silver. Silver is the preferred conductive particle for most uses. Alternatively, carbon black or graphite may also be used, alone or in combination with metal particles.

The average particle size of the metal or carbon or graphite particle can vary over a wide range but, is preferably in the range of from about 1 micron to about 50 microns, more preferably from about 2 microns to about 20 microns. If the average particle size of the metal particles is less than about 1 micron, the electrical properties may be adversely affected. In other words, if the metal particles are too fine, the resistivity of the composition may be too high. If the average particle size of the metal particles is above about 50 microns, then the composition will be too difficult to apply to the substrate. For example, the composition will tend to clog up during a silk screening process or the like.

Other minor conventional components may be added to the conductive composition. These include viscosity modifying agents and defoaming surfactants. The viscosity of the final conductive composition of this invention for screen printing is preferable from about 8,000 to about 25,000 centipoises at 30° C. (Brookfield RVT Spindle #6 at 20 rpm) in order to be screen printable.

The compositions of this invention may be applied to substrates by a variety of techniques, such as silk screening, spraying or brushing. Once the conductive polymer thick film has been applied to the substrates it is cured at between about 93° C. and 135° C. for a time sufficient to complete curing with good adhesion.

The conductive compositions of the present invention may be applied to conventional rigid or flexible substrates. Whether the substrate is flexible or rigid in nature, the substrate may or may not have to be pretreated or precoated with any other substance before applying the present composition.

EXAMPLE 1

Preparation of an Aqueous Polymer Thick Film-forming Composition Using Silver Flake A 40% solution of Peox in water was made using a cowles mixer. This solution was then vigorously hand mixed with the rest of the mixture's components as identified in the table hereinbelow. The resulting mixture was then passed through a three roll mill to provide the desired film-forming composition.

| Composition Component | Weight in Parts Per 100/Wt |
| --- | --- |
| Peox (Polyethyloxyazoline) (1) | 2.80 |
| AW875 (2) | 20.38 |
| Silver Flake (3) | 55.25 |
| $H_2O$ | 16.22 |
| Diethylene Glycol Mono Ethyl Ether | 5.22 |
| BYK020 (4) | 0.13 |

The properties of the film-forming composition were as follows:

| | |
| --- | --- |
| Electrical resistivity | 19 milliohms/sq. @ 1.0 mil |
| Printability | Very good |
| Adhesion | <2 in resistance |
| Print Quality | Good |

EXAMPLE 2

Preparation of Another Aqueous Polymer Thick Film-forming Composition Using Silver Flake A 55% solution by weight of PVP K-30 in $H_2O$ was made using a cowles mixer. This solution was then agitated with the rest of the mixture's components as identified in the table hereinbelow. The resulting mixture was then passed twice through a three roll mill to provide the desired film-forming composition.

| Component | Parts per 100 |
| --- | --- |
| PVP (5) | 1.09 |
| AW875 | 28.15 |
| Ethylene Glycol | 7.52 |
| $H_2O$ | 1.96 |
| Witco 748 (6) | .6 |
| Triton CF-10 | .6 |
| Silver Flake | 60.08 |

The properties of the film-forming composition were as follows:

| | |
| --- | --- |
| Viscosity | 10,150 CPS |
| | (Brookfield # 6 spindle @ 20 rpm, 25° C.) |
| Resistivity | 17 milliohms/sq. @ 1.0 mil |
| Adhesion | <2 in resistance |
| Flexibility | |
| 1 crease | +10% |
| 3 crease | <+150% |

EXAMPLE 3

Preparation of an Aqueous Polymer Thick Film-forming Composition Using Carbon Particles A 55% solution of PVP K-30 in $H_2O$ was prepared using a cowles mixer. This solution was then agitated with the rest of the mixture's components as identified in the table hereinbelow. The resulting mixture was then passed twice through a three roll mill to provide the desired film-forming composition.

| Component | Parts per 100 |
| --- | --- |
| Carbon (XC-72) (8) | 6.26 |
| AW875 | 60.88 |
| Triton CF-10 | 2.60 |
| PVP K-30 | 2.46 |
| Ethylene Glycol | 16.31 |
| $H_2O$ | 10.34 |
| Witco 748 | 1.15 |

The properties of the film-forming composition were as follows:

| | |
| --- | --- |
| Resistivity | 1700 ohms/sq. @ 1.0 mil |
| Printability | Good |

The following is a list of sources for the various trademarks/tradenames used in the above three examples.

1) "Peox" is a water and solvent soluble polyethyloxyazoline previously available from Union Carbide, 39 Old Ridgebury Road, Danbury, Conn. 06817-0001.
2) "AW875" is a vinyl resin dispersed in water, available from Union Carbide, 39 Old Ridgebury Road, Danbury, Conn. 06817-0001.
3) "Silver flake" is available from Chemet Corporation, 52 Gardner Street, Attleboro, Mass. 02703.
4) "BYK02011 is a defoamer available from BYK Chemie USA, 524 South Cherry Street, Wallingford, Conn. 06492.
5) "PVP K-30" is a polyvinyl pyrrolidone polymer, soluble in $H_2O$, available from GAF Chemicals Corporation, 1361 Alps Road, Wayne, N.J. 07470.
6) Witco "Bubble Breaker 748" is a defoamer available from Witco Organics Division, 3230 Brookfield Street, Houston, Tex. 77045.
7) "Triton CF-10" is a surfactant available from Union Carbide, 39 Old Ridgebury Road, Danbury, Conn. 06817-0001.
8) "XC-72" is a carbon powder available from Cabot Corporation, 125 High Street, Boston, Mass. 02110.

In addition, as used in the above examples, the "adhesion" test refers to the percentage change in resistance after applying Scotch tape to a test pattern of the ink and then removing the tape and remeasuring the resistivity. Similarly, the "flexibility" test measures the percentage change after creasing the test pattern which was silk screened for each example.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety. All parts and percentages are by weight unless otherwise explicitly stated.

What is claimed is:

1. An aqueous conductive polymer thick film-forming and printable composition comprising:
   (a) about 0.25% to about 20% by weight of water-soluble thermoplastic polymer selected from the group consisting of polyethyloxazoline, polyvinyl pyrrolidone, polyvinyl alcohol, polyacrylamide, polyglycol, and polyacrylic acid;

(b) about 10 to 70% by weight of a water insoluble polymer dispersion in water, said dispersed polymer selected from the group consisting of polyurethane resin polymer, acrylic resin polymer, polyester resin polymer, and vinyl resin polymer;

(c) about 2% to about 20% by weight of at least one glycol compound drying-retarder agent;

(d) an effective electrically conducting amount of less than 90% by weight of conductive particles selected from the group consisting of conductive metal particles, carbon black particles, graphite particles, and combinations thereof; with the proviso that the amount of said carbon black particles, graphite particles, or combinations thereof do not exceed 40% by weight; and (e) an effective solvating amount of water to dissolve water-soluble thermoplastic polymer (a); each of said amounts being based upon the total weight of said composition.

2. The composition of claim 1 wherein said water-soluble thermoplastic polymers is polyethyloxazoline.

3. The composition of claim 1 wherein said water-soluble thermoplastic polymers is polyvinyl pyrrolidone.

4. The composition of claim 1 wherein said dispersed polymer is vinyl resin polymer.

5. The composition of claim 1 wherein said glycol drying-retarding agent is ethylene glycol.

6. The composition of claim 1 wherein said conductive particles are silver flake.

7. The composition of claim 1 additionally comprising viscosity modifying agents and defoaming surfactants.

8. The composition of claim 1 wherein said conductive particles are from about 1 micron to about 50 microns.

* * * * *